United States Patent [19]

Forschner et al.

[11] Patent Number: 5,159,127
[45] Date of Patent: Oct. 27, 1992

[54] PROCESS FOR CONVERTING PARAFFINS TO ALPHA OLEFINS

[75] Inventors: Thomas C. Forschner, Richmond; Thomas F. Brownscombe; Jiang-Jen Lin, both of Houston, all of Tex.

[73] Assignee: Shell Oil Company, Houston, Tex.

[21] Appl. No.: 803,761

[22] Filed: Dec. 5, 1991

Related U.S. Application Data

[63] Continuation of Ser. No. 576,237, Aug. 31, 1990, abandoned.

[51] Int. Cl.$^5$ .............................. C07C 4/06
[52] U.S. Cl. ................... 585/324; 585/653; 585/646; 585/647
[58] Field of Search ............. 585/648, 651, 324, 653, 585/645, 646, 647

[56] References Cited

U.S. PATENT DOCUMENTS

| | | | |
|---|---|---|---|
| 2,882,244 | 4/1959 | Milton | 252/455 |
| 2,950,240 | 8/1960 | Weisz | 585/324 |
| 3,293,193 | 12/1966 | Krahler et al. | 260/2 |
| 3,449,070 | 6/1969 | McDaniel et al. | 23/111 |
| 3,872,179 | 3/1975 | Andersen et al. | 585/651 |
| 4,159,970 | 7/1979 | Heckelsberg | 502/324 |
| 4,251,348 | 2/1981 | O'Rear et al. | 585/324 |
| 4,255,605 | 3/1981 | Dixon | 585/324 |
| 4,377,490 | 3/1983 | Shiraishi et al. | 252/188.3 |
| 4,424,116 | 1/1984 | Hettinger | 208/120 |
| 4,621,162 | 11/1986 | Delzer et al. | 585/651 |
| 4,929,791 | 5/1990 | Kaeding | 585/648 |
| 5,093,540 | 3/1992 | Forschner et al. | 585/645 |

Primary Examiner—Anthony McFarlane
Attorney, Agent, or Firm—Pamela J. McCollough

[57] ABSTRACT

This invention is a two step process for converting linear paraffins to linear alpha olefins. In the first step the paraffins are cracked to a mixture of alpha and internal olefins by use of a cracking catalyst of a zeolite in combination with an alkali(ne earth) metal compound wherein the sum of the amount of the alkali(ne earth) metal in the compound plus any metal cation exchanged into the zeolite is in excess of that required to provide a fully metal cation-exchanged zeolite. The resulting olefin-containing cracked product is then converted to a substantially alpha olefin-containing product by contact with ethylene and a disproportionation catalyst at disproportionation conditions. The resulting products contains only small amounts of aromatics.

28 Claims, No Drawings

PROCESS FOR CONVERTING PARAFFINS TO ALPHA OLEFINS

This is a continuation of application Ser. No. 07/576,237, filed Aug. 31, 1990, now abandoned.

FIELD OF THE INVENTION

This invention relates to a process for the conversion of paraffins to alpha olefins, particularly straight chain paraffins to straight chain alpha olefins.

BACKGROUND OF THE INVENTION

Zeolites are known as useful for the catalytic cracking of hydrocarbon feedstocks, particularly feedstocks containing feedstocks. The problem with the use of conventional zeolites as cracking catalysts is that they produce a variety of products: olefins, both branched and straight chain, aromatics, paraffins and other products resulting from dealkylation, aromatic side-chain scission, isomerization, condensation and disproportionation reactions. A catalytic cracking process that would produce only olefins in substantial quantities when combined with a subsequent ethenolysis process would be of commercial significance, since the resulting alpha olefins can be used as feedstocks to produce higher valued end products.

Olefins serve as feedstocks for the chemical industry. They can be converted to corresponding alcohols or aldehydes. Higher molecular weight alcohols can further be ethoxylated with ethylene or propylene oxide in the presence of a catalyst to form conventional detergents while lower molecular weight alcohols can be esterified with aromatic acids to form plasticizers. Alpha olefins are used as comonomers for high density polyethylene (HDPE) and linear low density polyethylene (LLDPE), intermediates for synthetic lube oils and lube oil additives, paper sizings and other specialty chemicals.

SUMMARY OF THE INVENTION

This invention relates a two step process for converting linear paraffins to alpha olefins. The first step comprises contacting said paraffins with a catalyst comprising a zeolite and an alkali(ne-earth) metal compound wherein the sum of the amount of the alkali(in-earth) metal in the compound plus any metal cation exchanged into the zeolite is in excess of that required to provide a fully metal cation exchanged zeolite. The product of this step contains only small amounts of aromatics and branched olefins. The cracked product is then converted to an olefin product containing primarly alpha olefins by contact with ethylene and a disproportionation catalyst at disproportionation conditions.

DETAILED DESCRIPTION OF THE INVENTION

The term "alkali(ne-earth) metal" as used hereinafter refers to a metal selected from the group consisting of alkali metal, alkaline earth metal and mixtures thereof, that is, it refers to alkali metal and/or alkaline earth metal and includes one or more alkali metals, one or more alkaline earth metals and two or more of a mixture of alkali metal(s) and alkaline earth metal(s).

Catalytic Cracking Step

The first step of the instant process comprises a catalytic cracking process for converting normal paraffins, that is straight chain aliphatic hydrocarbons to normal, that is straight chain olefins. Useful paraffins for the instant process range from $C_4$ to $C_{35}$ and above. These paraffins may be liquid at room temperature such as the $C_4$–$C_{20}$ group or solid at room temperature such as the $C_{21}$–$C_{35}$ and above group, or mixtures of both groups. The catalytic cracking is carried out in a gas and/or liquid phase at catalytic cracking conditions.

Any suitable reactor can be used for the catalytic cracking process of this invention. For example, a fixed bed of catalyst particles can be used, with paraffin feedstock passing through the catalyst bed at catalytic cracking conditions. Generally in commercial operations it is anticipated that a fluidized-bed catalytic cracking (FCC) reactor (preferably containing one or more risers) or a moving-bed catalytic cracking reactor (e.g., a Thermofor catalytic cracker) is employed, preferably a FCC riser cracking unit. Examples of such FCC cracking units are described in U.S. Pat. Nos. 4,377,470 and 4,424,116. Generally a catalyst regeneration unit (for removal of coke) is combined with the FCC cracking as is shown in the above-cited patents.

Specific operating conditions of the cracking operation depend greatly on the type of feed, the type and dimensions of the cracking reactor and the feed rate. Examples of operating conditions are described in the above-cited patents and in many other publications. In an FCC operation, generally the weight ratio of catalyst to feed ranges from about 2:1 to about 10:1, the contact time between oil feed and catalyst is in the range of about 0.2 to about 2 seconds, and the cracking temperature is in the range of from about 350° C. to about 650° C. Generally steam is added with the oil feed to the FCC reactor so as to aid in the dispersion of the oil as droplets. Generally the weight ratio of steam to oil feed is in the range of from about 0.05:1 to about 0.5:1. Pressures will typically range to about atmospheric to about five atmospheres. For fixed bed reactors temperatures and pressures are similar to those of an FCC reactor with liquid hourly space velocities typically ranging from about 0.1 to 10 hours$^{-1}$.

The Cracking Catalyst

The catalysts that are utilized in the cracking process step are described in co-pending U.S. patent applications Ser. No. 354,586, filed Jun. 22, 1989 and Ser. No. 387,265, filed Jul. 31, 1989, incorporated by reference herein.

Essentially any crystalline zeolitic aluminosilicate can be employed to prepare the cracking catalysts utilized in the instant process. The zeolites can include both synthetic and naturally occurring zeolites. Illustrative of the synthetic zeolites are Zeolite X, U.S. Pat. Nos. 2,882,244; Zeolite Y, 3,130,007; Zeolite A, 2,882,243; Zeolite L. Bel. 575,117; Zeolite D, Can. 611,981; Zeolite R, 3,030,181; Zeolite S, 3,054,657; Zeolite T, 2,950,952; Zeolite Z, Can. 614,995; Zeolite E, Can. 636,931; Zeolite F, 2,995,358; Zeolite O, 3,140,252; Zeolite W, 3,008,803; Zeolite Q, 2,991,151; Zeolite M, 2,995,423; Zeolite H, 3,010,789; Zeolite J, 3,001,869, Zeolite W, 3,012,853; Zeolite KG, 3,056,654; Zeolite SL, Dutch 6,710,729; Zeolite Omega, Can. 817,915; Zeolite ZK-5, 3,247,195; Zeolite Beta, 3,308,069; EU-1, 4,537,754; Zeolite ZK-4, 3,314,752; Zeolite ZSM-5, 3,702,886; Zeolite ZSM-11, 3,709,979; Zeolite ZSM-12, 3,832,449; Zeolite ZSM-20; 3,972,983; Zeolite ZSM-35, 4,016,245; Zeolite ZSM-50, 4,640,829; synthetic mordenite; the so-called ultrastable zeolites of U.S. Pat. Nos. 3,293,192 and 3,449,070; and the references cited therein, incorporated herein by reference. Other synthetic zeolites are described in the book "Zeolite Molecular Sieves-Structure, Chemistry and Use, " by Donald W. Breck. 1974, John Wiley & Sons, incorporated by reference herein. Illustrative of the naturally occurring crystalline zeolites are analcime, bikitaite, edingtonite, epistilbite, levynite, dachiardite, erionite, faujasite, analcite, paulingite, noselite, ferrierite, heulandite, scolecite, stilbite, clinoptilolite, harmotone, phillipsite, brewsterite, flakite, datolite, chabazite, gmelinite, cancrinite, leucite, lazurite, scolecite, mesolite, ptilolite, mordenite, nepheline, natrolite, scapolite, thomsonite, gismondine, garronite, gonnardite, heulandite, laumontite, levynite, offretite, yugawaralite. Descriptions of certain naturally occurring zeolites are found in the aforementioned book by Breck, in the book "Molecular Sieves-Principles of Synthesis and Identification", R. Szostak, Van Nostrand Reinhold, New York, 1989, both incorporated by reference herein, and in other known references. These zeolites may be in the hydrogen form or may be partially or fully exchanged with ammonium or metal ions.

As used herein, the term "compound" as applied to alkali(ne-earth) metal refers to the combination of alkali(ne-earth) metal with one or more elements by chemical and/or physical and/or surface bonding, such as ionic and/or covalent and/or coordinate and/or van der Waals bonding, but specifically excludes that bonding involved between an alkali(ne-earth) metal and a zeolite when such alkali(ne-earth) metal is located in a cation exchange site of the zeolite. The term "ionic" or "ion" refers to an electrically charged moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions. The term "oxidic" refers to a charged or neutral species wherein an element such as an alkali(ne-earth) metal is bound to oxygen and possibly one or more different elements by surface and/or chemical bonding. Thus, an oxidic compound is an oxygen-containing compound, which also may be a mixed, double, or complex surface oxide. Illustrative oxidic compounds include, by way of non-limiting example, oxides (containing only oxygen as the second element), hydroxides, nitrates, sulfates, carboxylates, carbonates, bicarbonates, oxyhalides, etc, as well as surface species wherein the alkali(ne-earth) metal is bound directly or indirectly to an oxygen either in the substrate or the surface. "Surface" as applied to zeolites and the instant cracking catalysts refers to external surface as well as the internal pore surface, the internal surface being both the surface of the macro pores resulting from the agglomeration of individual particles or crystallites as well as the surface of the mesopores and micropores and supercages that result from the intrinsic zeolite crystal structure. The term "salt" as used herein is meant to encompass a single salt as well as mixtures of two or more salts. The term "alkali metal" is used herein as a descriptor of the elements of Group IA of the Periodic Table of the Elements (Li, Na, K, Rb, Cs, Fr). The term "alkaline earth metal" is used herein as a descriptor of the elements of Group IIA of the Periodic Table of the Elements (Be, Mg, Ca, Sr, Ba, Ra). Alkali(ne-earth) metal herein does not refer to the element in the metallic or zero valent state, but rather is a shorthand use for the element in the positive valent state, that is, it will be understood to be combined as a salt, compound, complex, etc. The term "basic" refers to having the characteristic of a base; e.g., when placed in a solution, a basic material will have a pH consistent with a base rather than an acid and, if a catalyst, will catalyze chemical reactions that are catalyzed by bases.

The alkali(ne-earth) metal salts that are suitable for preparing the cracking catalysts utilized in the instant process are any salts that can be dissolved in a suitable impregnating solution or which can be melted to form their own impregnating solution or which can be sublimed and condensed on the zeolite. Illustrative but non-limiting examples of suitable salts are alkali(ne-earth) metal bicarbonates, carbonates, chlorates, perchlorates, cyanides, hydroxides, iodates, nitrates, nitrites, sulfates, hydrogen sulfates, sulfites, dithionates, thiosulfates, alkoxides, carboxylates, sulfonates, iodates, halides and the like. Of the alkali(ne-earth) salts that can be utilized to make the cracking catalysts, the hydroxide salts, particularly of alkali metals, are less preferred for providing the major portion of the alkali (ne earth) compound since these strongly basic salts in high concentrations can contribute to a degradation of the crystallinity of the zeolite. Salts which can be solubilized in a suitable solution are preferred. Preferred salts are those which have an oxygen-containing anion or oxyanion or which can be precipitated in situ with oxyanion. Useful salts are those which decompose at least in part upon calcination in the presence of the zeolite to provide an alkali(ne-earth) metal-oxygen-containing moiety (e.g., Na-O-, Ca-O-, etc.), that is, produce an oxidic compound. When the alkali(ne-earth) metal salt is associated with an anion which does not contain oxygen it is necessary that the salt be precipitated in situ with a suitable oxyanion, or alternatively, after impregnation, the subsequent calcination is carried out in an oxygen-containing atmosphere to cause the salt to react with the oxygen to provide the alkali(ne-earth) metal-oxygen-containing moiety, that is, produce an alkali(ne-earth) metal oxidic compound. Decomposition can be indicated by the evolution of gases such as carbon oxides, nitrogen oxides, sulfur oxides etc. Decomposition will also be indicated by disappearance at least in part of the particular anionic form associated with the alkali(ne-earth) metal in the impregnation liquid. For example, when carboxylates and alkoxides are calcined the carboxylate and alkoxide moiety associated with the alkali(ne-earth) metal will decompose giving off carbon oxides and/or water and/or hydrocarbons, thereby disappearing at least in part. Particularly preferred salts to be used in an impregnating solution are (alkali) carbonates nitrates and carboxylates. Mixtures of alkali(ne-earth) metal salts, that is, two or more salts with differing anions, differing cations or differing anions and cations can be utilized to prepare the impregnated zeolite.

One method that can be used to prepare the cracking catalysts utilized in the instant process involves the use of molten alkali(ne-earth) metal salt to impregnate the zeolite. In this method a suitable salt, that is, one melting below about 850° C., is melted and the zeolite is added to the molten salt or the molten salt is added to the zeolite causing the molten salt to impregnate the pores of the zeolite. A very suitable impregnation technique is to utilize that amount of molten salt that is equal to or less than that amount of molten salt that will just fill the pores of the zeolite. Alternatively, zeolite particles can be immersed in a molten salt bath to cause impregnation of the molten salt into the zeolite followed by separation of the excess molten salt from the zeolite, say by filtration, centrifugation or washing. Alternatively, zeolite particles can be coated with finely divided particles of a suitable alkali(ne-earth) metal salt and heated to above the melting point of the salt, causing the molten salt to impregnate the pores of the zeolite. Many other methods, such as fluid bed impregnation or spraying molten salt or solid salt onto zeolite in a rotating kiln will be obvious to one skilled in the art. After impregnation, the impregnated zeolite is calcined to produce the cracking catalyst utilized in the instant process. The calcining temperature may be the same or lower than the impregnating temperature but frequently it is higher. Drying is not required when the molten salt technique is utilized, but may be utilized to remove residual water remaining in the zeolite. The impregnation and calcination can be carried out in one continuous step or sequence. The alkali(ne-earth) metal nitrates and carboxylates are particularly suitable for use in the molten impregnation method.

Another method is to use a sublimable alkali(ne-earth) metal salt. In this method a suitable salt is sublimed at above its sublimation temperature to produce a vaporous salt and the resulting vapor is contacted with the zeolite maintained at a temperature near or below the sublimation temperature of the salt thereby causing the vapor to condense upon and within the pores of the zeolite thereby impregnating it. Calcination follows to prepare the cracking catalysts utilized in the instant process. Drying before calcination is not required in this case, but may be utilized to remove residual water in the zeolite. The impregnation and calcination can be carried out in one continuous step or sequence.

Most conveniently and preferably, solutions of alkali(ne-earth) metal salts are used to impregnate the zeolites. The solvents utilized to dissolve the salts may be organic or inorganic. The only requirement is that the desired salt be soluble in the particular solvent. Hydroxylic solvents are preferred. Water is a particularly preferred solvent. The lower alkanols are also particularly suitable for use with salts having strong basicity in water in order to minimize base-zeolite structure interactions during the impregnation process. Organic solvents are particularly useful as solvents for alkali(ne-earth) metal salts which have organic ionic components such as carboxylate, sulfonate, alkoxide, etc. Organic solvents are also useful for inorganic alkali(ne-earth) metal salts. Alkal(ine earth) metal salts having a low solubility in an organic solvent can be used with that solvent to provide small, but well controlled amounts of alkali(ne earth) metal to the zeolite while minimizing solvent-base-zeolite structure interactions. Illustrative, but non-limiting examples of organic solvents include alcohols, including polyhydric alcohols, ethers, esters, ketones, amides, sulfoxides and chloro-/fluorohydrocarbons such as the various freons. Specific illustrative examples include methanol, ethanol, glycol, dimethyl ether, methyl acetate, methylethyl ketone, dimethyl formamide ("DMF"), dimethyl sulfoxide ("DMSO"), N-methyl pyrrolidone ("NMP"), hexamethylphosphoramide ("HMPA"), dichlorodifluoromethane, methyl chloride, ethylene dichloride, ethylene carbonate, etc. Illustrative, but non-limiting examples of inorganic solvents include water, liquid ammonia, liquid carbon dioxide, liquid sulfur dioxide, carbon disulfide, carbon tetrachloride, etc. Mixtures of solvents which are mutually miscible may be utilized.

When the cracking catalyst comprises a zeolite-alkaline earth metal compound, a preferred variation on the impregnation technique comprises impregnating the zeolite with a soluble salt of an alkaline earth metal salt, followed by contact or reimpregnation with a precipitating agent, such as a suitable solubilized anion, that will form a precipitate in situ with alkaline earth metal ion. For example, a zeolite is first impregnated with an aqueous solution of barium or calcium nitrate or chloride. Then the impregnated zeolite, without intermediate drying and/or calcining is contacted with an aqueous solution of ammonium sulfate or hydroxide, causing barium or calcium sulfate or hydroxide to precipitate within the zeolite. This resultant material is then dried as necessary and optionally calcined. Gaseous precipitating agents may also be utilized. For example, after a zeolite is first impregnated with an aqueous solution of alkaline earth metal nitrate, it is then contacted with or without intermediate drying with gaseous amonia or dimethylamine, resulting in the precipitation of or conversion to the alkaline earth metal hydroxide. Preferred precipitating agents are those which produce an oxidic compound or a compound which is converted to an oxidic compound upon calcination.

Single or multiple impregnations may be used. When multiple impregnations are used intermediate drying steps, optionally followed by precipitation and/or calcination may be utilized. Generally any amount of impregnating liquid can be used in the impregnation process. For example, the zeolite can be dipped into a large excess (compared to the pore volume of the zeolite), removed and shaken of excess liquid. Alternatively, an amount of impregnating liquid considerably less than the pore volume can be sprayed onto an agitated bed of zeolite. For purposes of economy, control and other reasons, the volume of impregnating liquid will preferably range from about the pore volume to about four or five times, preferably about twice the pore volume of the zeolite to be impregnated. Alternatively, a "dry" impregnation technique is utilized wherein just that amount of impregnating solution is used which will just fill the pores of the zeolite. In another embodiment, baskets of zeolite material are dipped into a vat of impregnating solution, removed, dried and optionally calcined.

The concentration of alkali(ne-earth) metal salts in the impregnating solution is not critical and is selected, inter alia, on the basis of the zeolite used, the amount of ion exchange capacity present in the zeolite, the degree of basicity of the final product desired, the impregnation solvent used and the type of impregnation utilized, that is, multiple or single. Concentrations of alkali(ne-earth) metal salt(s) in the impregnating solution will typically range from about 0.01 moles per liter to the solubility limit of the salt(s). A suitable range is from about 0.01 to about 20 moles per liter, more preferably from about 0.1 to about 10 moles per liter.

The amount of alkali(ne-earth) metal which is impregnated into the zeolite must be in excess of that which would provide a fully cation-ion exchanged zeolite. For example, if the starting zeolite were completely in the hydrogen form and had an ion exchange capacity of 12% (basis $Na_2O$), then the equivalent amount of alkali(ne-earth) metal impregnated (basis $Na_2O$) must exceed the 12%. If the starting zeolite were one which had already been 80% exchanged with a metal cation, the amount of alkali(ne-earth) metal to be added by impregnation would be in excess of that amount required to exchange the remaining 20%. If the starting zeolite were fully metal cation exchanged, then any amount of alkali(ne-earth) metal in the impregnating solution would suffice. It is to be understood that impregnation of a partially or fully cation-exchanged zeolite will most likely result in some counter ion exchange between the impregnating alkali(ne-earth) metal cation(s) and the cations already present in the zeolite, but the resulting catalyst will still be within the scope of the instant invention in having an excess of alkali(ne-earth) metal present over the amount exchanged into the fully exchanged zeolite. When the amount of impregnating solution that is utilized is such that after impregnation no excess solution is removed, then the amount of alkali(ne-earth) metal salt in the impregnating solution will be the same as the amount impregnated into the zeolite. When an amount of impregnating solution is used that requires that an excess amount of solution must be removed, for example, by filtration or centrifugation, from the impregnated zeolite after impregnation, then the amount of alkali(ne-earth) metal in the impregnating solution will exceed the amount of alkali(ne-earth) metal impregnated into the zeolite. In this latter case, the amount of alkali(ne-earth) metal impregnated into the zeolite can be determined by a knowledge of concentration of alkali(ne-earth) metal in the impregnating solution before the impregnation, the concentration of alkali(ne-earth) metal in the excess solution removed from the impregnated zeolite and the amount of solution remaining after impregnation (the excess). Alternatively, the impregnated zeolite can be analyzed for alkali(ne-earth) metal content.

In general it is preferred to have a slight excess of alkali(ne-earth) metal present. When considering as a basis for calculation the zeolite having no cations exchanged therein, the preferred catalysts will have the sum of the alkali(ne-earth) metal in the alkali(ne-earth) metal compound and any metal cation exchanged into the zeolite being greater than 1, preferably greater than about 1.05, more preferably greater than about 1.1, even more preferably greater than about 1.15, even more preferably greater than about 1.2, even more preferably greater than about 1.5, even more preferably greater than about greater than about 2 times the amount required to provide a fully cation-exchanged zeolite (or times the exchange capacity). When considering the fully cation-exchanged zeolite as a basis for calculation, the amount of alkali(ne-earth) metal in the alkali(ne-earth) metal compound is greater than zero, preferably greater than about 0.05, more preferably greater than about 0.1, even more preferably greater than about 0.15, even more preferably greater than about 0.2, even more preferably greater than about 0.5, and even more preferably greater than about 1 times the amount of alkali(ne-earth) metal that would be required to provide a fully metal cation-exchanged zeolite (or times the exchange capacity).

After impregnation utilizing an impregnating solution or a subsequent precipitating solution, the impregnated zeolite is dried to remove the solvent of the impregnating and/or precipitating solution. The drying conditions are not critical to the instant invention. Drying may be carried out at atmospheric pressure, superatmospheric pressure or under vacuum. It also may be carried out by passing a dry (with regard to the impregnating solvent) gas over a bed of the zeolite. Drying temperatures will depend upon the solvent used. For those solvents that are liquid at low temperatures, such as liquid carbon dioxide or liquid sulfur dioxide, the drying temperature can be relatively low, that is, below room temperature. For the more conventional solvents which are liquid at or above room temperature, higher temperatures will be used. For these solvents temperatures will typically range from about room temperature to about 200° C. In most cases drying temperatures will be less than about 200° C., preferably less than 150° C. Drying times are dependent upon the drying temperature and pressure, typically from about one minute to about twenty hours, although longer or shorter times can be utilized. Drying atmospheres and pressures are normally not critical. The drying atmosphere may be neutral, oxidizing, reducing or a vacuum.

After drying to remove an impregnating solvent or after impregnation by means of a molten or vaporous salt, the impregnated zeolite is optionally calcined at elevated temperatures. Calcination conditions will range from about 150° C. to about 850° C. preferably from about 200° C. to about 750° C., and more preferably from about 200° C. to about 600° C. Calcining times are dependent on the calcining conditions selected and typically range from about one minute to about twenty hours, although longer or shorter times can be utilized. Calcining conditions and times are also adjusted according to the thermal stability. Calcination conditions should not be so extreme as to cause extreme loss of zeolite crystallinity. Calcining atmospheres may be neutral, oxidizing or reducing. When the impregnating salt has an anionic component which does not contain oxygen, an oxygen-containing calcining atmosphere is preferably utilized. Neutral atmospheres such as provided by nitrogen and oxidizing atmospheres such as provided by air are preferred.

When using an impregnation or an impregnating/precipitating solution, the drying and calcining steps may be combined into one integrated process step. In this combined step the impregnated zeolite is heated through the lower temperatures at a rate slow enough that physical disruption of the zeolite does not occur due to rapid volatilization of the solvent from the impregnation. After the solvent has been removed, the zeolite is then heated to the desired calcining temperature, maintained for the desired calcining time and then cooled to room temperature. Calcining (and drying) can be carried out in situ during the operation of a catalytic process in a catalytic reactor.

The exact form of the alkali(ne-earth) metal after calcination is not known. Without intending to limit the scope of the instant invention, it is believed that the alkali(ne-earth) metal(s) is present as one or more alkali(ne-earth) metal oxidic compounds. It is speculated that the alkali(ne-earth) metal compound(s) are probably in the form of a surface oxide or multiple surface oxides with the zeolite, in particular with the aluminum and/or silicon and/or oxygen of the zeolite lattice, possibly in combination with species contained in or formed from the impregnation solution or during the calcination process.

The calcination contributes to the production of a catalyst which is basic and this basic nature is thought to derive from the particular nature of the alkali(ne-earth) metal compound present after calcination. However, those catalysts produced by precipitation with a basic precipitating agent are within the scope of the instant invention, even without calcination taking place. The basic nature of these materials can be seen from the fact that instant cracking catalysts when placed in a solvent produce effects that are basic rather than acidic in nature. This can been seen by the use of suitable chemical or electrochemical indicators.

The basicity of the cracking catalysts can be determined in various ways. For example, it can be determined by measuring the extent to which various base-catalyzed reactions are carried out in the presence of of the instant cracking catalysts. Another method is to place the instant cracking catalyst in a solvent and measure the resulting pH by use of chemical or electrochemical indicators. A specific example would involve placing 20 mg of catalyst in 2 g of water and using a pH meter or pH paper to measure the resulting pH. Another method is to use various indicators in non-aqueous solutions and compare the indicator response caused by the instant cracking catalysts with the indicator response caused by selected reference samples. Suitable indicators are 4-nitroaniline or 4-chloroaniline dissolved in dimethyl sulfoxide ("DMSO") or benzene (@ 0.1 g/cc). Examples of indicator responses with various reference samples is shown in Table 1.

TABLE 1

| Reference | 4-nitroaniline/DMSO | 4-chloroaniline/benzene |
|---|---|---|
| NaNH$_2$ | very dark blue | purplish brown |
| KOH | dark blue | cream |
| NaY-Zeolite | yellow | cream |
| amorphorous SiO$_2$ | faint yellow | cream |

In general terms the cracking catalysts utilized in the instant process comprise a basic, structured, that is a zeolitically structured, alkali(ne-earth) metal-containing aluminosilicate containing in compound form an excess of alkali(ne-earth) metal over that necessary to provide a fully metal cation-exchanged aluminosilicate. More specifically, the cracking catalysts comprise a zeolite and an alkali(ne-earth) metal compound, particularly an oxidic compound, wherein the sum of the amount of the alkali(ne-earth) metal in the compound plus any metal cation exchanged into the zeolite is in excess of that required to provide a fully metal cation-exchanged zeolite. The alkali(ne-earth metal) compound will be found deposited on the surface of the zeolite. The cracking catalysts will contain at least a portion of their pore volume in micropores in the range of from about three to about twelve angstroms. The cracking catalysts react as bases when placed in solvents and catalyze base-catalyzed reactions.

The cracking catalysts retain at 1.east a portion of a crystalline zeolite structure. The term "crystalline" is employed herein to designate an ordered structure capable of being detected by electrooptical or diffraction techniques, normally by X-ray diffraction, giving a consistent crystallographic pattern. Such an ordered structure can persist even after some of the structural silica or alumina is removed from the crystal lattice, as by leaching with acids, or with bases such as might occur during the impregnation process, or by other physical or chemical methods. Sometimes the ordered structure may become so attenuated by these or other means as to fail to diffract X-rays, but in such cases other electrooptical methods, such as electron beam diffraction may be utilized. In other cases the crystallite size may become so small that diffraction effects may become so diffuse that the amount of crystalline structure may be difficult to detect or determine. In this latter instance, however, the retention of a large surface area after chemical and/or physical processing will indicate the retention of a certain amount crystalline zeolite structure. Thus these latter materials are still structured aluminosilicates as opposed to amorphous aluminosilicates and are within the scope of the instant invention.

The cracking catalysts utilized in the instant process, alone or in combination with other catalytic components, may be distributed throughout an inert inorganic diluent which also may serve as a binder. Non-limiting examples of such diluents include aluminas, silicas, silica-aluminas, charcoal, pumice, magnesia, zirconia, keiselguhr, fullers, earth, silicon carbide, clays and other ceramics. In a preferred use of binders the instant zeolitic catalysts are intimately mixed a finely divided, hydrous, refractory oxide of a difficulty reducible metal. The term "hydrous" is used to designate oxides having structural surface hydroxyl groups detectable by infrared analysis. The preferred oxides are alumina, silica, magnesia, beryllia, zirconia, titania, thoria, chromia, and combinations thereof such silica-alumina, silica-magnesia, and the like. Naturally occurring clays comprising silica and alumina may also be utilized, preferably after acid treatment. The metal oxide can be combined with the instant cracking catalysts as a hydrous sol or gel, an an anhydrous activated gel, a spray dried powder or a calcined powder. In one modification a sol or solution of the metal oxide precursor such as an alkali(ne-earth) metal silicate or aluminate can be precipitated to form a gel in the presence of the cracking catalysts utilized in the instant process. When less hydrous forms of the metal oxide are combined with the instant cracking catalysts, essentially any method of effecting intimate admixture of the components may by utilized. One such method is mechanical admixture, e.g., mulling, which involves admixing the instant cracking catalysts in the form of a powder with the slightly hydrous, finely divided form of the metal oxide. The diluent or binder may be added to the instant cracking catalysts at any point in their preparation, that is, before, during or after impregnation, drying and/or calcination.

The cracking catalysts may also be further activated by the incorporation into the zeolite of additional alkali metal compounds or salts, followed by calcination. For example a cracking catalyst utilized in the instant process may be impregnated by an aqueous solution of an alkali metal hydroxide or carbonate, dried and calcined to provide an enhanced basic catalyst.

Ethenolysis Step

The product of the cracking which contains a substantial portion of internal olefins is converted into a product containing substantially alpha olefins by being contacted with ethylene in the presence of an olefin disproportionation catalyst. It should be appreciated that two molecules of internal olefins in the cracked product may in some instances disproportionate to produce other higher and lower internal olefinic products during the reaction of the internal olefins with ethylene. To distinguish the two possible reactions, it is convenient to call the disproportionation of the internal olefins with ethylene "ethenolysis".

In order to effect the ethenolysis reaction and to insure that the disproportionation of two internal olefins does not proceed to any significant extent, e.g., 5% or less, it is essential to provide an excess of ethylene in the first disproportionation (ethenolysis) zone. Generally, molar ratios of ethylene to internal olefins of at least 8:1 are satisfactory, although molar ratios of ethylene to internal olefins of at least 15:1 are preferred.

The ethenolysis reaction is conducted by contacting in liquid phase, ethylene, the cracking product, the catalyst and, if desired, a reaction diluent which is liquid at reaction temperature and pressure. Illustrative of suitable diluents are hydrocarbons free from aliphatic unsaturation such as saturated acyclic or alicyclic alkanes of from 6 to 12 carbon atoms, e.g., hexane, isooctane, decane and cyclohexane; and monoaromatic hydrocarbons of from 6 to 12 carbon atoms, e.g., benzene and toluene. In most instances, added diluent is used in amounts up to about 20 moles of diluent per mole of olefinic reactants. The ethenolysis reaction is conducted in an inert reaction environment so that the reaction conditions are substantially anhydrous and substantially oxygen-free.

The precise method of establishing ethylene/olefin/catalyst contact is not critical. In one modification, the entire amounts of reaction components are charged to an autoclave, and the reaction mixture is maintained with agitation at reaction temperature and pressure for the desired reaction period. Another modification comprises passing, in a continuous manner, the olefinic reactants in liquid phase solution in the reaction diluent through a reaction zone in which the catalyst is maintained. By any modification, the ethenolysis process is generally conducted at moderate temperatures and pressures. Suitable reaction temperatures range from about −30° C. to about 250° C., preferably from about 0° C. to about 200° C. and most preferably from about 10° C. to about 150° C. The precise pressure is not critical, so long as the reaction mixture is maintained substantially in a non-gaseous phase. Typical pressures vary from about 1 atmosphere to about 100 atmospheres. The alpha olefin enriched product can be used as such or further purified by conventional means such as distillation or fractional crystallization.

The Disproportionation Catalyst

The disproportionation catalyst used in the instant process is selected from the large number of catalysts known in the art for their disproportionation activity. Typically the disproportionation catalyst comprises tungsten, molybdenum and/or rhenium deposited on an inert support such as alumina, silica or silica-alumina. Other transition metals such as ruthenium, rhodium osmium and iridium have also found use as disproportionation catalysts. A variety of catalysts have been employed for conducting disproportionation reactions, such as those disclosed in U.S. Pat. No. 3,340,322, issued Sep. 5, 1967; U.S. Pat. No. 3,637,892, issued Jan. 25, 1972; U.S. Pat. No. 3,760,026, issued Sep. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966, all incorporated by reference herein. Optionally tetra alkyl (alkyl being $C_1$ to about $C_6$) tin compounds, such as tetrabutyl tin, are used as promoters.

Typically the catalysts are prepared by impregnating the porous support such as alumina and/or silica with solutions of rhenium, molybdenum and/or tungsten compounds, drying and calcining at temperatures ranging from about 200°–800° C. Alternately, rhenium, molybdenum and/or tungsten compounds can be mulled into powdered support material, the resultant material consolidated into pellets and dried and calcined at 200°–800° C. Other art recognized catalyst preparative methods are also suitable.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The following illustrative embodiments are provided for illustration and are not to be construed as limiting the invention.

ILLUSTRATIVE EMBODIMENT

1. Cracking Catalyst Preparation

The following zeolites were used to prepare the cracking catalysts used in the instant invention:

1. LZ-Y52 is a zeolite Y molecular sieve obtained from Union Carbide Corporation. It has a unit cell size of about 24.7, a silica to alumina molar ratio of about 4.7 and a sodium oxide content of about 13 wt. %.

2. USY is a ultrastable zeolite Y that has been dealuminated by a combination of ammonium ion exchange and steaming. It has a unit cell size of about 24.5, a silica to alumina molar ratio of about 6.8 and a sodium oxide content of about 2.5 wt. %.

3. SDUSY is a super dealuminated ultrastable zeolite Y that has been dealuminated by a combination of ammonium ion exchange, steaming and acid leaching. It has a unit cell size of about 24.2, a silica to alumina molar ratio of about 80 and a sodium oxide content of about <0.04 wt. %.

4. 13X is the sodium form of zeolite X molecular sieve obtained from Union Carbide Corporation. It has a unit cell size of about 25.0, a silica to alumina molar ratio of about 1.23 and a sodium oxide content of about 15 wt. %.

Utilizing the above described zeolite substrates, cracking catalysts used in the instant process were prepared as follows:

Preparation of Magnesium Oxide/13X A 70.9 gram portion of 13X zeolite was washed with deionized water and vacuum dried. The zeolite was then treated with 28 milliliters of an aqueous solution of magnesium nitrate hexahydrate (15.3 grams, 0.060 moles) and vacuum dried. The catalyst was then washed twice with 250 milliliters of 1N potassium hydroxide and dried under vacuum overnight.

Preparation of Magnesium Oxide/LZ-Y52 A 50.83 gram portion of LX-Y52 was washed three times with 250 milliters of deionized water and dried under vacuum. The zeolite was then slowly treated with 15 milliliters of an aqueous solution of magnesium nitrate hexahydrate (11.04 grams, 0.04305 moles). The catalyst was then dried under vacuum for 2 hours at 150° C., treated with 10 milliliters of water, and dried for an addition 2 hours. The sample was then washed twice with 250 milliliters of 1N potassium hydroxide and vacuum dried overnight at 150° C.

Preparation of Magnesium Oxide/USY A 40 gram sample of USY zeolite was impregnated with 15 milliliters of an aqueous solution of magnesium nitrate hexahydrate (8.8 grams, 0.034 moles) and then dried under vacuum. The catalyst was then washed twice with 250 milliliters of 1N potassium hydroxide and dried under vacuum at 150° C.

Preparation of Magnesium Oxide/SDUSY After being washed three times with 250 milliliters of deionized water and vacuum dried, a 60 gram portion of SDUSY was treated with 24 milliliters of an aqueous solution of magnesium acetate tetrahydrate (11.1 grams, 0.051 moles). After drying, the catalyst was washed twice with 250 milliliters of 1N potassium hydroxide and dried under vacuum overnight.

Preparation of Cesium Oxide/13X A 50 gram portion of washed 13X zeolite was impregnated with 54 milliliters of an aqueous solution of cesium oxalate (15.0 grams, 0.0423 moles). The catalyst was then dried overnight under vacuum.

Preparation of Cesium Oxide/LZ-Y52 After being washed and dried under vacuum, a 20.23 gram portion of LZ-Y52 zeolite was impregnated with 20 milliliters of a methanolic solution of cesium acetate (4.38 grams, 0.0228 moles). The catalyst was then dried under vacuum overnight at 150° C.

Preparation of Cesium Oxide/USY A 50 gram sample of USY was impregnated with 54 milliliters of an aqueous solution of cesium oxalate (15.0 grams, 0.0423 moles). The catalyst was then dried under vacuum overnight.

Preparation of Cesium Oxide/SDUSY A 74 gram sample of USY was impregnated with 80 milliliters of an aqueous solution of cesium oxalate (22.0 grams, 0.0622 moles). The catalyst was then dried under vacuum overnight.

Preparation of Calcium Oxide/LZ-Y52 After being washed and dried, 20.23 grams of LZ-Y54 zeolite were treated with 15 milliliters of an aqueous solution of calcium nitrate tetrahydrate (5.38 grams, 0.0228 moles). The catalyst was then dried in an oven at 400° C. for two hours. After cooling to room temperature, the catalyst was impregnated with 10 milliliters of 1N potassium hydroxide. After 10 minutes the catalyst was washed twice with 250 milliliters of 1N potassium hydroxide and dried overnight under vacuum.

Preparation of Barium Oxide/LZ-Y52 After being washed and dried, 20.23 grams of LZ-Y52 zeolite were treated with 20 milliliters of barium nitrate (5.95 grams, 0.0228 moles). After drying, the catalyst was washed twice with 250 milliliters of 1N potassium hydroxide and the catalyst was dried under vacuum overnight.

II. Catalytic Cracking Step

Catalytic cracking experiments were carried out in a stainless steel flow reactor (34 cm by 1.2 cm internal diameter). The feed was metered into the flow reactor by the use of a Beckman model 110 B pump. The nitrogen delivery rates were controlled by the use of regulators and the flow rates were measured with a wet test meter. The reaction products were first cooled with a water condenser as they exit the reactor and then were further condensed by the use of two cold traps operating at −75° C. In a typical experiment 20 milliliters of catalyst was loaded over a 10 millimeter bed of silicon carbide in the flow reactor. A second 10 millimeter silicon bed was placed on top of the catalyst bed to preheat the feed before it contacted the catalyst.

The catalysts were activated by calcination under a nitrogen purge of 50 liters per hour at 575° C. for at least one hour. After calcination the nitrogen flow rate was lowered to 22 liters per hour and the reactor was allowed to cool to the reaction temperature. Hexadecane feed was then pumped into the reactor at a rate of 2.5 liters per liter of catalyst per hour. The contents of the two traps were mixed and analyzed by GC and GC mass spectrometry. The analytical results are presented in Table 2. Conversions and selectivities are in weight percents.

TABLE 2

| CATALYST | Rxn Temp | Catalytic Cracking | | | | | |
|---|---|---|---|---|---|---|---|
| | | Conv | LAO | LIO | BIO | PAR | AROM |
| Na/Y | 550° C. | 94 | 6.5 | 8.6 | 23.0 | 30.0 | 34.9 |
| Basic MgO/13X | 550° C. | 19 | 27.7 | 51.8 | <1.0 | 18.5 | <1.0 |
| Basic MgO/LZ-Y52 | 550° C. | 36 | 24.8 | 49.3 | <1.0 | 23.7 | <1.0 |
| Basic MgO/USY | 550° C. | 12 | 41.7 | 40.0 | <1.0 | 16.3 | <1.0 |
| Basic MgO/SDUSY | 550° C. | 5 | 44.3 | 38.9 | <1.0 | 14.8 | <1.0 |
| Basic Cs$_2$O/13X | 550° C. | 18 | 22.1 | 49.45 | 2.0 | 25.4 | <1.0 |
| Basic Cs$_2$O/LZ-Y52 | 550° C. | 28 | 21.1 | 51.2 | <1.0 | 25.7 | <1.0 |
| Basic Cs$_2$O/USY | 550° C. | 9 | 38.1 | 42.5 | <1.0 | 17.4 | <1.0 |
| Basic Cs$_2$O/SDUSY | 550° C. | 4 | 42.2 | 42.5 | <1.0 | 13.3 | <1.0 |
| Basic CaO/LZ-Y52 | 550° C. | 36 | 23.3 | 48.4 | 2.0 | 25.3 | <1.0 |
| Basic BaO/LZ-Y52 | 550° C. | 6 | 39.9 | 47.5 | <1.0 | 10.6 | <1.0 |

Note: No branched alpha olefins were observed in products
LAO = Linear Alpha Olefins
LIO = Linear Internal Olefins
BIO = Branched Internal Olefins
PAR = Paraffins - excluding hexadecane feed
AROM = Aromatics

III. Disproportionation Catalyst

The disproportionation catalyst was prepared by impregnating 65 grams of KC-300 alumina extrudate (from Kaiser) with an aqueous solution of 45.5 milliliters of rhenium heptoxide (10 grams, 0.0206 moles). The impregnated alumina was then dried under vacuum for 12 hours at 122° C. The catalyst was then activated in a flow reactor at 550° C. for 1 hour in air at a flow rate of 15 liters per hour. The catalyst was then calcined under nitrogen at the same temperature and flow rate for an additional 2 hours. The flow reactor was then sealed and brought into a glove (oxygen and/or water free. The calculated rhenium content of the alumina was 11.7% based on the amount of rhenium heptoxide used.

Catalysts based on tungsten or molybdenum would also be suitable.

IV. Ethenolysis Step

In these experiments the product of the cracking reaction above was reacted with ethylene in the presence of a disproportionation catalyst in order to convert the olefin product into one containing substantially alpha olefins. A rhenium oxide on alumina catalyst prepared as described above was used as the disproportionation catalyst.

The ethenolysis reactions were run in batch mode using 100 milliliter autoclaves. Catalyst and cracking product were loaded into the autoclave in the drybox. Tetrabutyl tin was used as an activator (0.002 grams per gram of rhenium catalyst). The autoclave was pressured with ethylene to maintain 800 psig and the reactor was heated to the reaction temperature. After a run time of about 2 hours, the contents were analyzed by GC and GC mass spectrometry. The GC data is provided in Table 3. The aliphatics numbers correspond to the weight percent within a given carbon number fraction of both paraffin and olefin. The percent alpha olefin (AO) within a given fraction was also calculated and shown in the table.

TABLE 3

Product Distributions* for the Ethenolysis of the Cracking Products over "Basic" Zeolites

| Catalyst | Temp | Component | Carbon Number | | | | | | | | | | | |
|---|---|---|---|---|---|---|---|---|---|---|---|---|---|---|
| | | | 4 | 5 | 6 | 7 | 8 | 9 | 10 | 11 | 12 | 13 | 14 | 15 |
| Basic Cs$_2$O/LZ-Y52 | 450 | Aliphatics | b | 9.73 | 13.43 | 14.70 | 14.01 | 13.19 | 11.28 | 9.16 | 7.11 | 5.83 | 1.50 | 0.01 |
| | | (% AO | b | 91.05 | 82.80 | 74.51 | 70.99 | 67.20 | 60.38 | 61.72 | 55.04 | 45.52 | 65.19 | b) |
| Basic Cs$_2$O/LZ-Y52 | 550 | Aliphatics | b | 2.30 | 5.67 | 9.64 | 12.23 | 14.58 | 15.38 | 14.31 | 12.33 | 10.61 | 2.9 | 0.01 |
| | | (% AO | b | 81.67 | 78.13 | 74.25 | 76.25 | 75.86 | 74.29 | 73.96 | 67.74 | 65.45 | 75.10 | b) |
| Basic MgO/LZ-Y52 | 550 | Aliphatics | 2.93 | 6.03 | 8.68 | 10.79 | 12.65 | 14.37 | 13.60 | 11.69 | 9.64 | 7.78 | 3.61 | 1.14 |
| | | (% AO | 91.10 | 90.01 | 84.70 | 79.51 | 75.72 | 72.39 | 72.38 | 68.50 | 61.20 | 48.00 | 71.30 | b) |
| Basic CaO/LZ-Y52 | 550 | Aliphatics | 5.72 | 10.64 | 12.79 | 13.06 | 12.43 | 12.46 | 10.80 | 8.45 | 6.91 | 5.31 | 1.38 | 0.01 |
| | | (% AO | 90.60 | 85.33 | 81.92 | 76.03 | 74.26 | 70.91 | 67.36 | 67.15 | 59.23 | 47.07 | 69.43 | b) |
| Basic CaO/LZ-Y52 | 550 | Aliphatics | 2.97 | 5.61 | 10.62 | 11.18 | 12.06 | 13.00 | 12.01 | 10.73 | 9.08 | 7.17 | 3.67 | 2.20 |
| | | (% AO | 92.91 | 88.69 | 87.58 | 87.11 | 85.18 | 85.18 | 83.77 | 82.60 | 78.78 | 74.57 | 84.12 | 90.0) |
| Basic BaO/LZ-Y52 | 550 | Aliphatics | 1.32 | 3.73 | 6.09 | 7.93 | 9.64 | 11.57 | 12.09 | 12.85 | 12.42 | 11.81 | 6.04 | 4.44 |
| | | (% AO | 98.8 | 98.8 | 96.12 | 93.45 | 95.09 | 95.10 | 96.48 | 96.48 | 93.15 | 90.00 | 88.10 | b) |
| Basic MgO/13X | 550 | Aliphatics | 0.51 | 11.11 | 13.92 | 13.76 | 11.98 | 10.37 | 8.52 | 5.85 | 4.32 | 3.41 | 0.82 | b |
| | | (% AO | 98.8 | 78.2 | 60.72 | 57.0 | 53.4 | 50.7 | 53.4 | 48.5 | 58.4 | 70.1 | 52.2 | b) |

*Product distribution given in weight percent. Percent AO corresponds to the percent AO within a given carbon fraction. b-below detection limits

What is claimed is:

1. A process for converting paraffins to alpha olefins which comprises:
   (a) contacting at a temperature ranging from about 350° C. to about 650° C. said paraffins with a cracking catalyst comprising a zeolite and an alkali(ne-earth) metal compound which has not been exchanged into the zeolite to produce an internal olefin-containing product, and
   (b) contacting at a temperature ranging from about −30° C. to about 250° C. the product of step (a) with ethylene and a disproportionation catalyst to form alpha olefins.

2. The process of claim 1 wherein in step (b) the temperature ranges from about 0° to about 200° C.

3. The process of claim 2 wherein in step (b) the temperature ranges from about 10° C. to about 150° C.

4. The process of claim 1 wherein the disproportionation catalyst comprises a metal selected from molybdenum, tungsten, rhenium and mixtures thereof supported on a support selected from the group consisting of alumina, silica and silica-alumina.

5. The process of claim 4 wherein the disproportionation catalyst is rhenium supported on alumina.

6. The process of claim 4 wherein a tetraalkyl tin compound is used a promoter for the disproportionation catalyst.

7. The process of claim 4 wherein in the cracking catalyst said alkali(ne-earth) metal compound is present in an amount whereby the alkali(ne-earth) metal is in excess of about 0.05 times the amount of alkali(ne-earth) metal required to provide a fully metal cation-exchanged zeolite.

8. The process of claim 7 wherein in the cracking catalyst the alkali(ne-earth) metal is in excess of about 0.1 times the amount of alkali(ne-earth) metal required to provide a fully metal cation exchanged zeolite.

9. The process of claim 8 wherein in the cracking catalyst the alkali(ne-earth) metal is in excess of about 0.2 times the amount of alkali(ne-earth) metal required to provide a fully metal cation exchanged zeolite.

10. The process of claim 9 wherein in the cracking catalyst the alkal (ne-earth) metal is in excess of about 0.5 times the amount of alkali(ne-earth) metal required to provide a fully metal cation-exchanged zeolite.

11. The process of claim 10 wherein in the cracking catalyst the alkali(ne-earth) metal is in excess of about 1 times the amount of alkali(ne-earth) metal required to provide a fully metal cation-exchanged zeolite.

12. The process of claim 4 wherein in the cracking catalyst the compound is an oxidic compound.

13. The process of claim 1 wherein the paraffins have carbon numbers ranging from about 4 to about 35.

14. The process of claim 13 wherein the paraffins have carbon numbers ranging from about 4 to about 20.

15. The process of claim 1 wherein the zeolite in the cracking catalyst is a zeolite Y.

16. The process of claim 1 wherein in step (b) the mole ratio of ethylene to internal olefins contained in the product of step (a) is greater than 8:1.

17. A process for converting paraffins to alpha olefins which comprises:
   (a) contacting at a temperature ranging from about 350° C. to about 650° C. said paraffins with a cracking catalyst comprising a zeolite which has been impregnated with an alkali(ne-earth) metal compound which has not been exchanged into the zeolite, and calcined at a temperature ranging from about 150° C. to about 850° C. to produce an internal olefin-containing product, and
   (b) contacting at a temperature ranging from about −30° C. to about 250° C. the product of step (a) with ethylene and a disproportionation catalyst to form alpha olefins.

18. The process of claim 17 wherein in step (b) the temperature ranges from about 0 to about 200° C.

19. The process of claim 18 wherein in step (b) the temperature ranges from about 10° C. to about 150° C.

20. The process of claim 17 wherein the disproportionation catalyst comprises a metal selected from molybdenum, tungsten, rhenium and mixtures thereof supported on a support selected from the group consisting of alumina, silica and silica-alumina.

21. The process of claim 20 wherein the disproportionation catalyst is rhenium supported on alumina.

22. The process of claims 20 wherein a tetraalkyl tin compound is used as promoter for the disproportionation catalyst.

23. The process of claim 17 wherein the paraffins have carbon numbers ranging from 4 to about 35.

24. The process of claim 23 wherein the paraffins have carbon numbers ranging from 4 to about 20.

25. The process of claim 17 wherein in the cracking catalyst the zeolite is a zeolite Y.

26. The process of claim 17 wherein the cracking catalyst has been calcined at a temperature ranging from about 200° C. to about 750° C.

27. The process of claims 17 wherein the cracking catalyst has been calcined in a nitrogen- or oxygen-containing atmosphere.

28. The process of claim 17 wherein in step (b) the mole ratio of ethylene to internal olefins contained in the product of step (a) is greater than 8:1.

* * * * *